(12) United States Patent
Ampulski et al.

(10) Patent No.: US 9,126,173 B2
(45) Date of Patent: Sep. 8, 2015

(54) PRETREATMENT OF BIOMASS USING THERMO MECHANICAL METHODS BEFORE GASIFICATION

(75) Inventors: Robert S. Ampulski, Fairfield, OH (US); John T. Turner, West Chester, OH (US); Joel K. Monteith, Bethel, OH (US); Freya Kugler, Conifer, OH (US)

(73) Assignee: Sundrop Fuels, Inc., Longmont, CO (US)

( * ) Notice: Subject to any disclaimer, the term of this patent is extended or adjusted under 35 U.S.C. 154(b) by 469 days.

(21) Appl. No.: 13/429,847

(22) Filed: Mar. 26, 2012

(65) Prior Publication Data
US 2013/0248767 A1 Sep. 26, 2013

(51) Int. Cl.
*B01J 8/12* (2006.01)
*C10J 3/62* (2006.01)
(Continued)

(52) U.S. Cl.
CPC .. *B01J 8/087* (2013.01); *B01J 8/12* (2013.01); *C07C 29/1518* (2013.01); *C10G 3/00* (2013.01); *C10J 3/485* (2013.01); *C10J 3/62* (2013.01); *C10J 3/74* (2013.01); *C10L 1/06* (2013.01); *D21B 1/12* (2013.01); *B01J 2208/00132* (2013.01); *B01J 2208/00504* (2013.01); *B01J 2208/00513* (2013.01); *C10J 2300/0906* (2013.01); *C10J 2300/0916* (2013.01); *C10J 2300/1246* (2013.01); *C10J 2300/1269* (2013.01); *C10J 2300/1665* (2013.01); *C10L 9/083* (2013.01); *Y02E 50/18* (2013.01); *Y02E 50/32* (2013.01)

(58) Field of Classification Search
CPC .... C10J 3/50; C10J 2200/15; C10J 2200/152; C10J 2200/156; C10J 2300/0906; C10J 2300/0909

USPC .............................................. 48/61
See application file for complete search history.

(56) References Cited

U.S. PATENT DOCUMENTS 5,196,460 A 3/1993 Lora et al.
5,747,320 A 5/1998 Saha et al.
(Continued)

FOREIGN PATENT DOCUMENTS

WO WO 2011159154 A1 12/2011
WO WO 2013191897 A1 12/2013

OTHER PUBLICATIONS

U.S. Appl. No. 61/119,062, Dec. 2, 2008, Stites.
(Continued)

*Primary Examiner* — Matthew Merkling
(74) *Attorney, Agent, or Firm* — Rutan & Tucker, LLP

(57) ABSTRACT

An integrated plant generates syngas from biomass, where the integrated plant includes a Thermo Mechanical Pulping (TMP) process, a biomass gasifier, a methanol synthesis process, and a liquid fuel generation process. Biomass is received as a feedstock in the TMP process. The biomass is pre-treated in the TMP process for subsequent supply to the biomass gasifier by using a combination of heat, pressure, moisture, and mechanical agitation that are applied to the biomass to make the biomass into a pulp form. The TMP process breaks down a bulk structure of the received biomass, at least in part, by applying steam to degrade bonds between lignin and hemicellulose from cellulose fibers of the biomass. Next, the broken down particles of the biomass are reacted in a biomass gasification reaction at a temperature of greater than 700 degrees C. to create syngas components, which are fed to a methanol synthesis process.

12 Claims, 5 Drawing Sheets

(51) Int. Cl.
*C10J 3/74* (2006.01)
*C10L 1/06* (2006.01)
*B01J 8/08* (2006.01)
*C07C 29/151* (2006.01)
*C10J 3/48* (2006.01)
*D21B 1/12* (2006.01)
*C10G 3/00* (2006.01)
*C10L 9/08* (2006.01)

(56) References Cited

U.S. PATENT DOCUMENTS

| | | | |
|---|---|---|---|
| 5,769,934 | A | 6/1998 | Ha et al. |
| 5,882,905 | A | 3/1999 | Saha et al. |
| 6,172,204 | B1 | 1/2001 | Sarkanen et al. |
| 6,555,350 | B2 | 4/2003 | Ahring et al. |
| 6,660,506 | B2 | 12/2003 | Nguyen et al. |
| 6,899,791 | B2 | 5/2005 | Sabourin |
| 7,109,005 | B2 | 9/2006 | Eroma et al. |
| 7,300,540 | B2 | 11/2007 | Sabourin et al. |
| 7,625,728 | B2 | 12/2009 | Eroma et al. |
| 7,713,381 | B2 | 5/2010 | Sabourin et al. |
| 7,846,294 | B2 | 12/2010 | Sabourin et al. |
| 7,919,070 | B2 | 4/2011 | Stites et al. |
| 8,003,352 | B2 | 8/2011 | Foody et al. |
| 8,028,945 | B2 | 10/2011 | Gingras |
| 8,057,639 | B2 | 11/2011 | Pschorn et al. |
| 8,088,832 | B2 * | 1/2012 | Melnichuk et al. .......... 518/700 |
| 8,157,195 | B2 | 4/2012 | Gingras |
| 8,187,849 | B2 | 5/2012 | Larsen |
| 8,192,854 | B2 | 6/2012 | Borole |
| 8,378,151 | B2 | 2/2013 | Perkins et al. |
| 8,961,628 | B2 | 2/2015 | Ampulski et al. |
| 2002/0159929 | A1 * | 10/2002 | Kaneko et al. ................ 422/190 |
| 2008/0022595 | A1 * | 1/2008 | Lemaire et al. ................ 48/209 |
| 2009/0221814 | A1 | 9/2009 | Pschorn et al. |
| 2009/0286295 | A1 | 11/2009 | Medoff et al. |
| 2010/0137459 | A1 | 6/2010 | Stites et al. |
| 2010/0237291 | A1 | 9/2010 | Simmons et al. |
| 2010/0270505 | A1 | 10/2010 | Gallaspy et al. |
| 2010/0273899 | A1 | 10/2010 | Winter |
| 2011/0111456 | A1 | 5/2011 | Medoff et al. |
| 2011/0150722 | A1 | 6/2011 | Stites et al. |
| 2011/0162376 | A1 * | 7/2011 | Guo ................ 60/746 |
| 2012/0042567 | A1 * | 2/2012 | Rawls et al. .................... 44/606 |
| 2012/0047794 | A1 | 3/2012 | Bartek et al. |
| 2014/0249237 | A1 | 9/2014 | Ferraro et al. |

OTHER PUBLICATIONS

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

"StakeTech—First Pulping System Receives Full Acceptance", May 14, 1996, 2 pages. Publisher: BusinessWire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/mdf/manufacture.html.

Lam, PS "Steam Explosion of Biomass to Produce Durable Wood Pellets", University of British Columbia, May 2011, Downloaded from Internet Oct. 21, 2013 from https://circle.ubc.ca/bitstream/id/ubc_2011_fall_lam_paksui.pdf.

International Search Report and Written Opinion for International Patent Application No. PCT/US2013/044143, 18 pages. International Searching Authority/US, Alexandria, VA US.

Final Office Action for U.S. Appl. No. 13/531,318 mailed May 29, 2014, 9 pages. U.S. Patent & Trademark Office, Alexandria, VA US.

Non-Final Office Action for U.S. Appl. No. 13/531,318 mailed Oct. 25, 2013, 9 pages. U.S. Patent & Trademark Office, Alexandria, VA US.

Restriction Requirement for U.S. Appl. No. 13/531,318 mailed May 20, 2013, 7 pages. International Searching Authority/US, Alexandria, Virginia USA.

Notice of Allowance for U.S. Appl. No. 13/531,318 mailed May 29, 2014, 14 pgs., U.S. Patent & Trademark Office, Alexandria, Virginia USA.

* cited by examiner

| Stage of Carbonization and Volatile compounds produced from slow pyrolysis | | 1. Beginning of the operation (Water driven off from biomass) | 2. 1st period of gas-evolution (gases containing $O_2$) | 3. Evolution of hydrocarbons begins | 4. CnHm gases | 5. Dissociation period | 6. Hydrogen period |
|---|---|---|---|---|---|---|---|
| Temperature (Deg. C) | | 150-200 | 200-280 | 280-380 | 380-500 | 500-700 | 700-900 |
| Percentage of carbon in the left remaining in the char | | 60 | 68 | 78 | 84 | 89 | 91 |
| Composition of non-condensable gas, vol % | $CO_2$ | 68 | 66.5 | 35.5 | 31.5 | 12.2 | 0.4 |
| | CO | 30.5 | 30 | 20.5 | 12.3 | 24.5 | 9.6 |
| | Hydrogen | 0.0 | 0.2 | 5.5 | 7.5 | 42.7 | 80.7 |
| | Hydrocarbons | 2 | 3.3 | 36.5 | 48.7 | 20.4 | 8.7 |
| Calorific value of 1 m³ of gas, kcal | | 1100 | 1210 | 3920 | 4780 | 3630 | 3160 |
| Condensable constituents of the volatile gas | | Water vapor | Water vapor and acetic acid | Acetic acid, wood naptha, light tar | Large quantities of viscous tar | Large quantities of tar mixed with paraffin | Scanty condensate |
| Quantity of gas | | Very small | Moderate | Considerable | Considerable | Scanty | Very small |

FIG. 4

PRETREATMENT OF BIOMASS USING THERMO MECHANICAL METHODS BEFORE GASIFICATION

FIELD

The invention generally relates to pre-treatment of biomass using thermo mechanical methods before gasification and in an embodiment specifically to an integrated plant that uses this biomass to produce a liquid fuel from the biomass.

BACKGROUND

Prior to the emergence of the petrochemical industry, wood distillation was the primary source of industrially important organic chemicals, but most wood distillation plants were closed by 1950. A resurgence in interest in wood distillation products arose in the late 1900's, as efforts were focused on renewable energy sources as an alternative to petroleum (Gade 2010). Much of this renewed interest has been in the use of fast pyrolysis to produce bio-oil, or "bio-crude." In this process, biomass of small particle size is rapidly heated (1-2 sec), at high temperature (500° C.), and the vapor is rapidly cooled, to yield ~70% liquid bio-oil. The bio-oil is an acidic, highly oxygenated, product that is subject to aging and must be further refined to produce satisfactory liquid fuels. To date, no large-scale commercialization of bio-oil or other integrated plant to economically make bio-fuel has been achieved.

SUMMARY

In an embodiment, an integrated plant generates syngas from biomass where the integrated plant includes a Thermo Mechanical Pulping process, a biomass gasifier, a methanol synthesis process, and a liquid fuel generation process. Biomass is received as a feedstock in the Thermo Mechanical Pulping process. The biomass is pre-treated in the Thermo Mechanical Pulping process for subsequent supply to a biomass gasifier by using a combination of heat, pressure, moisture, and mechanical agitation that are applied to the biomass to make the biomass into a pulp form. The thermo mechanical pulping process breaks down a bulk structure of the received biomass, at least in part, by applying steam to degrade bonds between the lignin and the hemi-cellulose from cellulose fibers of the biomass. Next, the broken down particles of the biomass are reacted in a rapid biomass gasification reaction at a temperature of greater than 700 degrees C. to create syngas components, which are fed to a methanol synthesis process. The methanol may be used to produce a number of liquid fuels.

BRIEF DESCRIPTION OF THE DRAWINGS

The multiple drawings refer to the example embodiments of the invention.

FIG. 4 illustrates a table of volatiles produced in an example torrefaction unit and/or TMP unit that are segregated into two or more operational stages.

Figure 1:
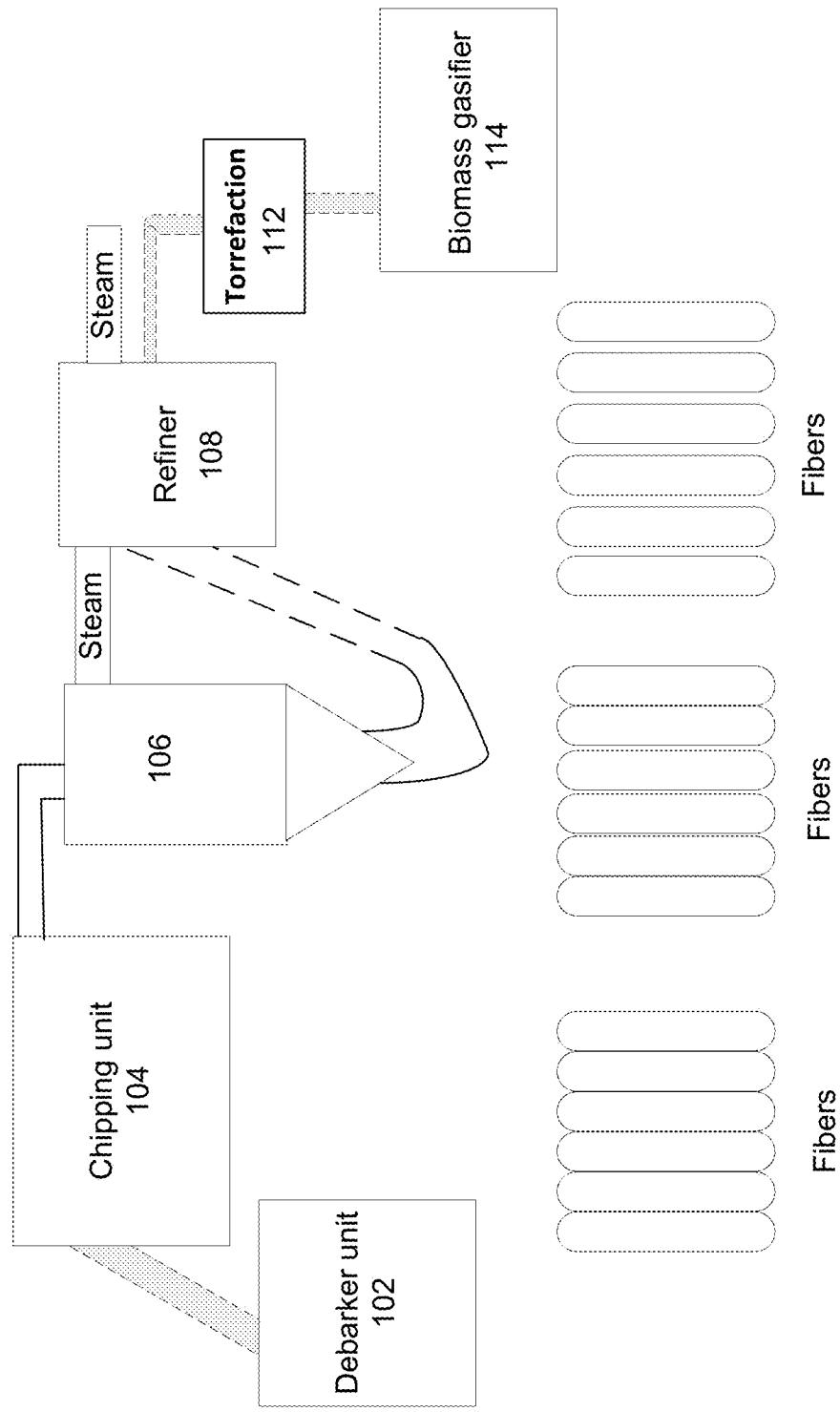
FIG. 1 illustrates a flow schematic of an embodiment of a Thermo Mechanical Pulping unit having an input cavity to receive biomass as a feedstock, a steam supply input, and two or more stages to pre-treat the biomass for subsequent supply to a biomass gasifier.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific chemicals, named components, connections, types of heat sources, etc., in order to provide a thorough understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

In general, a number of example processes for and apparatuses associated with a pre-treatments of biomass are described. The following drawings and text describe various example implementations for an integrated plant using the pre-treatments of biomass. In an embodiment, the integrated plant contains a Thermo Mechanical Pulping unit and a biomass gasifier to generate syngas from biomass. The Thermo Mechanical Pulping unit at least has an input cavity to receive biomass as a feedstock, a steam supply input, and two or more stages to pre-treat the biomass for subsequent supply to a biomass gasifier. The two or more stages use any combination of heat, pressure, moisture, and mechanical agitation that are applied to the biomass to make the biomass into a pulp form. The Thermo Mechanical Pulping process breaks down the bulk structure of the biomass, at least in part, by applying steam from the steam supply input and potentially mechanical force to soften and degrade bonds between the lignin and the hemi-cellulose from cellulose fibers of the biomass. The biomass gasifier has at least a reactor configured to react particles of the biomass broken down by the two or more stages of the Thermo Mechanical Pulping unit and those biomass particles are subsequently fed to a feed section of the biomass gasifier. A possible biomass gasifier implementation has a high temperature steam supply input and one or more regenerative heaters. In the presence of the steam, the particles of the biomass broken down by the Thermo Mechanical Pulping unit are reacted in the reactor vessel in a rapid biomass gasification reaction at a temperature of greater than 700 degrees C. in less than a five second residence time in the biomass gasifier to create syngas components, including hydrogen ($H_2$) and carbon monoxide ($CO$), which are fed to a methanol ($CH_3OH$) synthesis reactor.

In an embodiment, steam is applied to biomass at a temperature above a glass transition point of the lignin to soften the lignin so the cellulose fibers of the biomass can easily be mechanically stripped apart from the biomass in chip mass form. This temperature of the glass transition point of the lignin is generally above 150° C. for dry chips of biomass. These temperatures can be lower in the presence of water. The TMP process may be a two or more stage process similar in some aspects to the one used to make medium density fiber board (MDF). In the first stage, the TMP process uses whole chips of biomass including leaves, needles, bark, and wood. The chips of biomass are heated to about 160° C. using the steam at about 90 psi (6.2 bar) for about 120 seconds. No additional moisture is added to the chips of biomass beyond the steam condensate and pump seal water that may be used as a process aid in the process. In the second stage, the softened chips of biomass are sent directly to a refiner unit to mechanically strip apart the biomass and make pulp using refining energy in the range of less than about 300 to 100 kwh/odmt (kilowatt hours/oven dry metric ton) and preferably energy less than 100 kwh/odmt. One skilled in the art will understand parts and aspects of many of the designs discussed below within this illustrative document may be used as stand-alone concepts or in combination with each other.

FIG. 1 illustrates a flow schematic of an embodiment of a Thermo Mechanical Pulping unit having an input cavity to receive biomass as a feedstock, a steam supply input, and two or more stages to pre-treat the biomass for subsequent supply to a biomass gasifier.

A pre-treatment of biomass occurs using a thermo mechanical method before the gasification of the biomass in the biomass gasifier. Thermo Mechanical Pulping, also known as TMP, is one such thermo mechanical method that can be used where the pulp is produced by processing wood chips using heat (thus thermo) and a mechanical refining movement (thus mechanical). The Thermo Mechanical Pulping unit may be a multiple stage process.

Prior to the TMP, the logs of trees may first be stripped of their bark into a debarker unit 102 and then converted into small chips by a chipper unit 104. An on-site or off-site mill uses wood (trees) as the biomass fiber source and removes the bark. Removal of the bark is done in the debarker unit 102. Bark contains relatively few usable fibers for paper production because it darkens the pulp. In the gasification process in an embodiment, the debarker unit 102 removes the bark from the biomass and feeds all or just portions of the removed bark as well as leaves, needles and other carbon organics to the Thermo Mechanical Pulping unit to be turned into pulp and fed subsequently as biomass particles into the biomass gasifier to be turned into syngas components in a rapid biomass gasification reaction. In the alternative, the plant just feeds all of the biomass directly into the chipper 104 and thus has no need for a debarker unit 102. Thus, the thermally decomposing stage 106 and the refiner unit stage 108 can be configured to receive and process all or just portions of the removed bark as well as leaves, needles and other carbon organics to be used as the biomass to be turned into syngas components. Note if any bark is removed, then the bark may also be segregated and burned, along with other unusable plant material, as the fuel source for a traditional wood burning boiler to generate steam for use in the TMP stages, and/or in the biomass gasifier 114.

As discussed, the logs of wood potentially other biomass of needles, bark, leaves, etc., are chipped before being processed further to loosen and free the fibers in the biomass. The biomass chipper unit 104 has shearing tools to chip the logs of wood and other plant parts used as biomass feedstock and cooperating screens to provide some uniformity to the size of the chips of biomass. Woody biomass arrives at the later TMP pulping stages in the form of chips that can range in average size from 0.5 to 3" in length and a tight consistency in length and diameter is not required for the feed stock chips. It is relatively easy and energy efficient to create chips with this size before pulping and subsequent gasification.

The wood may also be steamed prior to the grinding/shearing to the make chips. These chips may have a large moisture content and will be thermally heated from the steam and then a mechanical force is applied to the wood chips in a shearing or grinding action, which generates additional heat and water vapor that softens the lignin, which aids in separating the individual fibers of the wood in the later stages. The soften structure of the woody biomass can be easier to chip.

The next step is the Thermo Mechanical Pulping processing, where heat, pressure, moisture, and mechanical force are applied to the fibrous chips of biomass to make pulp.

The pulp may be a lignocellulosic fibrous material prepared by chemically and/or mechanically separating cellulose fibers from wood, fiber crops, or waste paper. Wood pulp comes from softwood trees, such as spruce, pine, fir, larch and hemlock, and hardwood trees, such as eucalyptus, aspen and birch. Wood and other plant materials used to make pulp contain three main components (apart from water): cellulose fibers (used in other technologies for paper making), lignin (a three-dimensional polymer that binds the cellulose fibers together, which is chemically removed in the paper making field) and hemi-celluloses, (shorter branched carbohydrate polymers). The biomass contains cellulose fibers and hemi-cellulose that are held together with lignin. The aim of pulping is to break down the bulk structure of the fiber source, be it chip form, stem form, or other plant parts, into the small groups of fibers or even into individual constituent fibers.

The multiple stages in the Thermo Mechanical Pulping unit at least include a thermally decomposing stage 106 and a refiner unit stage 108. The Thermo Mechanical Pulping unit has an input cavity to receive biomass as a feedstock, a steam supply input, and two or more stages to pre-treat the biomass for subsequent supply to a biomass gasifier 114. The stages use a combination of heat, pressure, moisture, and mechanical agitation that are applied to the biomass to make the biomass into a pulp form. The thermo mechanical pulping process breaks down a bulk structure of the received biomass, at least in part, by applying steam from the steam supply input to soften the lignin and make it easier to degrade bonds between the lignin and the hemi-cellulose from cellulose fibers of the biomass.

Strength of the fibers is further impaired with the gasification's use of thermo mechanical pulping because the fibers are separated to potentially individual fibers and also cut to small dimensions. A lack of concern exists to maintain the strength of the fibers in the woody biomass chips compared to the paper pulping industry. The traditional TMP process tries to maintain the strength of the fibers to make particle board, newspapers, etc. In the current application of using the fibrous biomass in pulp form as a chemical reactant feedstock, the steam in connection with the mechanical force can be used to weaken the fibers and the fibers can then be cut to small dimensions because the fibers, lignin, and cellulose will eventually be thermally decomposed into syngas components. This process of TMP for gasification is less costly than producing paper with TMP because the gasification process does not require full length strong fibers as required for making paper or the traditional extra steps used to keep the strength of the fibers.

The Thermo Mechanical Pulping process also reduces the amount of energy required to produce particles of biomass compared to mechanical treatment alone. A major issue in the paper industry is that mechanical pulp mills use large amounts of energy, mostly electricity to power motors that turn the grinders. Steam treatment significantly reduces the total energy needed to make the pulp and eases the separation of the fibers. Thus, many advantages exist to the gasification of woody and other fibrous biomass to strip apart the fibers from the lignin.

The steam tube stage 106 has the input cavity to receive chips of the biomass. The steam tube stage 106 has a steam supply input applies steam into a vessel containing the chips of biomass at an elevated temperature of 100 to 200 degrees C., and preferably about 165 degrees C., at a pressure above atmospheric, such as around 90 psi, for a short period of time, such as approximately 2 minutes. The chips of biomass with the softened lignin are then fed from the steam tube stage 106 to the refiner unit stage 108 to further separate the fibers.

In the refiner unit stage 108 of the Thermo Mechanical Pulping unit, it is operated at the same pressure and temperature as the steam tube stage. Internally in the refiner unit stage 108, mechanical pulping mechanisms apply mechanical force to assist the steam in physically tearing the cellulose fibers one from another while the heat and pressure of the steam expands and blows apart the structure of the lignin, fiber and cellulose.

There are a number of different mechanical processes that can be used to separate the wood fibers. For example, manufactured grindstones with embedded silicon carbide or aluminum oxide or metal discs called refiner plates can be used to grind the biomass chips. Thus, the chips are steamed while being refined by the grindstones or metal discs to create the pulp. These chips of biomass have a large moisture content, are thermally heated from the steam, expanded by the elevated temperature and pressure, and then a mechanical force may also be applied to the wood chips in a crushing, shearing, vibrating, or grinding action, which generates additional heat and shredding action, which aids in separating the individual fibers from each other and the lignin.

The TMP unit reduces the biomass into smaller particle sizes that should be more easily and rapidly gasified. Fibers are long tubular strings of material, whereas chips are irregular spheres. The fibers compare to angel hair spaghetti, whereas chips are more like ravioli. Torn and shredded fibers may be preferred for the gasification process because they create a higher surface to volume ratio for the same amount of biomass. The higher surface area of the fibers traveling through the biomass gasifier 114 compared to a chip allows higher heat transfer to the biomass material and a more rapid thermal decomposition and gasification of all the molecules in the biomass. Thus, nearly all of the biomass material lignin, fiber, and cellulose completely gasify rather than some of the inner portions of the chip not decomposing to the same extent to that the crusted shell of a char chip decomposes.

A collection chamber at an outlet stage of the refiner unit stage 108 is used to collect the biomass reduced into smaller particle sizes and in pulp form, which should be more easily and rapidly gasified. The produced particles of biomass in pulp form include fibers in the form of long tubular strings of material that are torn and/or shredded. The biomass particles separated into fibers are preferred for the biomass gasification reaction in the biomass gasifier 114 because they create a higher surface to volume ratio for the same amount of biomass compared to chips of biomass, which allows higher heat transfer to the biomass material and a more rapid thermal decomposition and gasification of all the molecules in the biomass. The refiner unit stage 108 has a knife stage in the fiber separation unit that initially separates the fibers from the chips and may chop the fibers of the biomass to shorter lengths of 1-3 mm and then a high pressure steam fiber separation stage furthers the blowing apart of the loosely grouped fibers in the particles of biomass. The refiner unit produces fiber particles that on average are approximately 20-50 μm thick and 1-3 mm in length. In another embodiment, the fibers may have an equivalent spherical diameter of less than 3 mm.

In another embodiment, the Thermo Mechanical Pulping unit has a low-pressure steam supply input in a first stage and a high pressure steam supply in a second stage to pretreat the biomass for subsequent supply to a biomass gasifier. The multiple stages in the Thermo Mechanical Pulping unit at least include a first thermally decomposing stage 106 and a second refiner unit stage 108. The thermo mechanical pulping process breaks down a bulk structure of the received biomass, at least in part, by applying steam from the low-pressure steam supply input to degrade bonds between the lignin and the hemi-cellulose from cellulose fibers of the biomass. The thermally decomposing stage 106 has a low-pressure steam supply input applies steam into a vessel containing the chips of biomass at an elevated temperature of 100 to 150 degrees C., and preferably about 130 degrees C., at a pressure around atmospheric (15 psi) for a set period of time, such as approximately 10-30 minutes. The softened biomass may be then screened and cleaned. The chips of biomass with the softened lignin are then fed from the thermally decomposing stage 106 to the refiner unit stage 108 with its higher pressure to further separate the fibers.

In the second refiner unit stage 108 of the Thermo Mechanical Pulping unit, the pressure and temperature are raised in a chamber containing the chips of biomass with softened lignin to an increased temperature of at least twenty degrees, such as 150 C, greater than an operating environment of the vessel with chips of biomass in the thermally decomposing stage 106, and to an increased pressure greater than three times atmospheric in the chamber, such as 60 pounds per square inch (psi), but for a shorter duration than the set period of time in the thermally decomposing stage 106, such as less than 5 minutes. Internally in the refiner unit stage 108, mechanical pulping mechanisms apply mechanical force to assist the higher pressure steam in physically tearing the cellulose fibers one from another while the heat and pressure of the steam expands and blows apart the structure of the lignin, fiber and cellulose.

Figure 2:
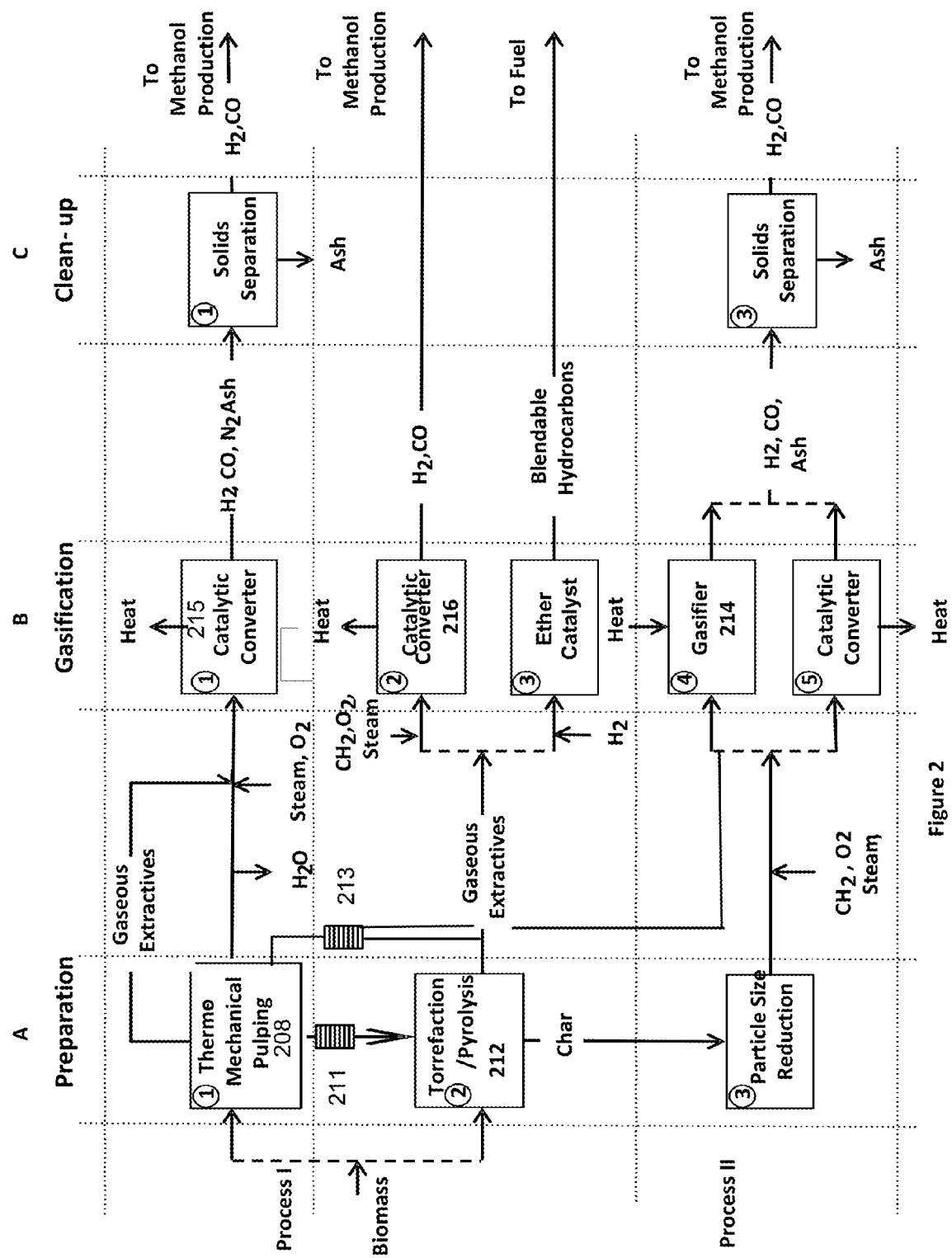
FIG. 2 illustrates a flow schematic of an embodiment of a Thermo Mechanical Pulping unit having a refiner unit stage that supplies particles of biomass in pulp form to either a torrefaction unit, or to the biomass gasifier, or to a catalytic converter.

FIG. 2 illustrates a flow schematic of an embodiment of a Thermo Mechanical Pulping unit having a refiner unit stage that supplies particles of biomass in pulp form to either a torrefaction unit, or to the biomass gasifier, or to a catalytic converter.

Overall, the Thermo Mechanical Pulping loosens and strips the fibers from the lignin. A conveying system coupled to a collection chamber at the outlet stage of the refiner unit stage 208 supplies particles of biomass in pulp form to either a torrefaction unit 212, or to the biomass gasifier 214, or to a catalytic converter 215. A majority of the initial lignin and cellulose making up the biomass in the receiver section of the steam tube stage in the TMP unit 208 remains in the produced particles of biomass but now substantially separated from the fibers in pulp form in the collection chamber at the outlet stage of the refiner unit stage 208.

In an embodiment, the collection chamber at an outlet stage of the refiner unit stage 208 is used to collect the biomass reduced into smaller particle sizes and in pulp form, and a conveyor system supplies the biomass in pulp form to a torrefication unit 212 to pyrolyze biomass at a temperature of less than 700 degrees C. for a preset amount of time to create off gases to be used in a creation of a portion of the syngas components, which are collected by a collection chamber and eventually fed to the methanol synthesis reactor. The collection chamber in the TMP unit 208 is configured to collect non-condensable hydrocarbons from any off gases produced from the biomass during the TMP process.

Figure 3:
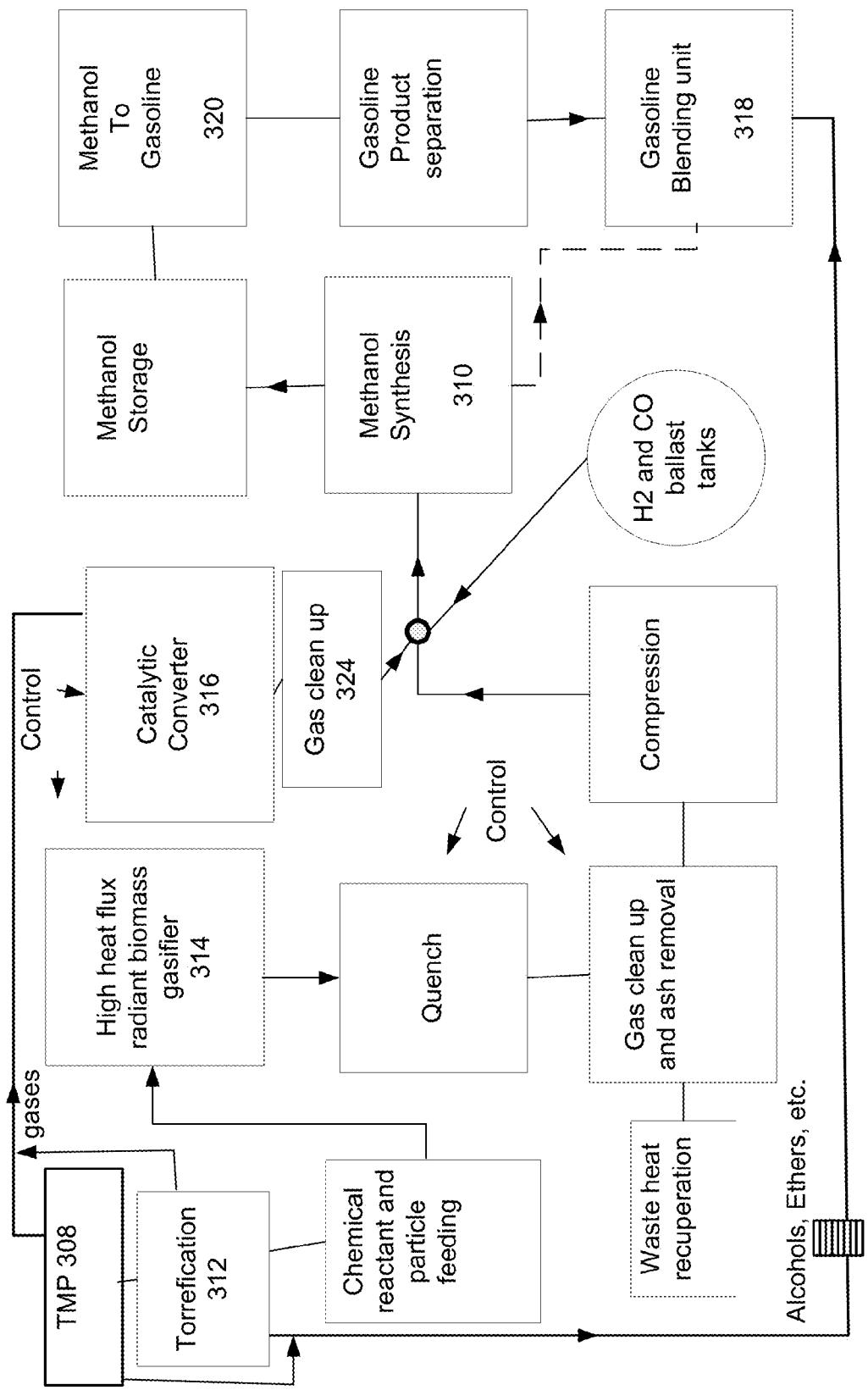
FIG. 3 illustrates an embodiment of a flow diagram of an integrated plant to generate syngas from biomass and generate a liquid fuel product from the syngas.

After the refiner unit stage 208, water is removed from the pulp in a water separation unit 211, for example a cyclone unit, and the reduced moisture content pulp made of loose fibers and separated lignin and cellulose may be fed to a torrefaction unit 212 to under go multiple stages of torrefaction. Condensable hydrocarbons including alcohols, ethers, and other C5 hydrocarbons may be separated by a filter unit 213 from the water removed from the pulp and then the condensable hydrocarbons are sent to a gasoline blending unit FIG. 3 illustrates an embodiment of a flow diagram of an integrated plant to generate syngas from biomass and generate a liquid fuel product from the syngas.

As discussed, the condensable hydrocarbons separated by the filter unit from the water removed from the pulp may be sent to a gasoline blending unit 318. The gasoline blending unit 318 is configured to blend gasoline produced from a methanol to gasoline (MTG) reactor 320, which receives its methanol derived from the syngas components in a proper ratio fed to the methanol synthesis reactor 310 from the biomass gasifier 314, the catalytic converter 316, and H2 and CO ballast tanks. The gasoline blending unit 318 is configured to blend the gasoline from the methanol to gasoline reactor 320 with condensable volatile materials including C5+ hydrocarbons collected during the pyrolyzation of the biomass in the torrefication unit 312 and those separated by the filter unit, which removes water from the pulp produced in the TMP unit 308.

One or more gas collection tanks in the TMP unit 308 may collect non-condensable hydrocarbons from any off gases produced from the biomass during the TMP process and send those non-condensable hydrocarbons with any collected in the torrefication unit 312 to a catalytic converter 316.

In another embodiment, the reduced moisture content pulp may go directly from TMP unit 308 to the biomass gasifier 314, a torrefaction unit 312, or to a catalytic converter 316. Generally, the pulp goes to the torrefaction unit 312 and then onto the biomass gasifier 314.

The refiner unit stage in the TMP unit 308 has a collection chamber to collect the biomass particles with separated fiber and feeds them to a feeding system for the biomass gasifier 314. The TMP unit 308 is configured to receive two or more types of biomass feed stocks, where the different types of biomass include 1) soft woods, 2) hard woods, 3) grasses, 4) plant hulls, and 5) any combination that are blended and thermo mechanically processed into a homogenized torrefied feedstock within the TMP unit 308 that is subsequently collected and then fed into the biomass gasifier 314. The torrefaction unit 312 assists in making a biomass feed system that is feedstock flexible without changing out the physical design of the feed supply equipment or the physical design of the biomass gasifier via at least particle size control of the biomass particles produced from refiner unit stage 308. The general compositions of biomass types that can be blended, for example, include:

| Component | Wood | Non-wood |
|---|---|---|
| Cellulose | 40-45% | 30-45% |
| Hemi cellulose | 23-35% | 20-35% |
| Lignin | 20-30% | 10-25% |

The biomass gasifier 314 has a reactor configured to react particles of the biomass broken down by the two or more stages of the Thermo Mechanical Pulping unit and those biomass particles are subsequently fed to a feed section of the biomass gasifier 314. The biomass gasifier 314 has a high temperature steam supply input and one or more regenerative heaters, and in the presence of the steam the particles of the biomass broken down by the Thermo Mechanical Pulping unit are reacted in the reactor vessel in a rapid biomass gasification reaction at a temperature of greater than 700 degrees C. in less than a five second residence time in the biomass gasifier 314 to create syngas components, including hydrogen (H2) and carbon monoxide (CO), which are fed to a methanol (CH3OH) synthesis reactor 310. In the gasifier, the heat transferred to the biomass particles made of loose cellulose fibers, lignin, and hemicellulose no longer needs to penetrate the layers of lignin and hemicellulose to reach the fibers. Alternatively, even if some lignin and hemicellulose remains on the fibers making larger fiber bundles, the high temperature and pressure inside the biomass gasifier 314 more easily expands and blows apart the bonds of the structurally weaker component parts of the biomass. In some embodiments, the rapid biomass gasification reaction occurs at a temperature of greater than 1000 degrees C. to ensure the removal tars from forming during the gasification reaction. However, due to the TMP action, formation of tars during biomass gasification can occur on a consistent basis as low as at the 700 degree C. temperature. Thus, a starting temperature of 700 degrees but less than 950 degrees is potentially a significant range of operation for the biomass gasifier. All of the biomass gasifies more thoroughly and readily. The TMP pre-treatment to the woody biomass improves the biomass gasifier reactor performance of syngas components yield and less tars while maintaining substantially all of the original carbon content contained in the biomass.

The biomass gasifier 314 may have a radiant heat transfer to particles flowing through the reactor design with a rapid gasification residence time, of the biomass particles of 0.1 to 5 seconds and preferably less one second, of biomass particles and reactant gas flowing through the radiant heat reactor, and primarily radiant heat from the surfaces of the radiant heat reactor and particles entrained in the flow heat the particles and resulting gases to a temperature in excess of generally 700 degrees C. and preferably 1300° C. to produce the syngas components including carbon monoxide and hydrogen, as well as keep produced methane at a level of ≤1% of the compositional makeup of exit products, minimal tars remaining in the exit products, and resulting ash. In some embodiments, the temperature range for biomass gasification is greater than 800 degrees C. to 1400 degrees C. In some embodiments, the temperature range for biomass gasification is greater than 900 degrees C. to 1450 degrees C. In some embodiments, the temperature range for biomass gasification is greater than 1000 degrees C. In some embodiments, the temperature range for biomass gasification is greater than 700 degrees C. The biomass particles separated into fibers and used as a feed stock into the radiant heat reactor conveys the beneficial effects of more effective heat transfer of radiation to the biomass particles and increased gasifier yield of generation of syngas components of carbon monoxide and hydrogen for a given amount of biomass fed in, and improved process hygiene via decreased production of tars and C2+ olefins compared to chips of biomass. A control system for the radiant heat reactor 314 matches the radiant heat transferred from the surfaces of the reactor to a flow rate of the biomass particles to produce the above benefits.

The cellulose fibers, lignin, and hemicellulose produced from the TMP unit can be further processed using torrefaction and/or extractive removal, followed by biomass gasification at temperatures greater than 900 degrees C. in a biomass gasifier 314.

Alternative ways exist to create the syngas. The biomass is supplied to the Thermo-Mechanical Pulping unit 208, water is removed from the pulp, and the pulp is exposed to steam and oxygen and then supplied to a catalytic converter 215. The catalytic converter 215 produces H2, CO, and Ash. A solids separator removes the Ash from the gas stream. Synthesis gas of H2 and CO from the gasifier and the catalytic converter 215 exit gases are sent to methanol synthesis reactors.

Other methods of TMP may include chemithermomechanical pulping, in which the wood chips can be pre-treated with sodium carbonate, sodium hydroxide, and other chemicals prior to refining with equipment similar to a mechanical mill. The conditions of the chemical treatment are much less vigorous (lower temperature, shorter time, less extreme pH) than in a chemical pulping process since the goal is to make the fibers easier to refine, not to remove lignin as in a fully chemical process.

Referring to FIG. 2, the plant uses any combination of the three ways to generate syngas for methanol production. 1) The TMP unit and/or torrefaction of biomass causes off gases to be fed to a catalytic converter 216 that can generate hydrogen and carbon monoxide for methanol production. 2) The biomass gasifier 214 gasifies biomass at high enough temperatures to eliminate a need for a catalyst to generate hydrogen and carbon monoxide for methanol production. 3) Alternatively, a lower temperature catalytic conversion of particles of biomass may be used to generate hydrogen and carbon monoxide for methanol production. Similarly, the thermal mechanical pulping process and torrefaction process may be used to generate condensable hydrocarbons for use in gasoline blending to increase the octane of the final gasoline product.

The torrefaction unit 212 pyrolyzes biomass from the TMP unit 208 to create off gases to be used in a creation of a portion of the syngas components fed to the methanol synthesis reactor and a char remains to be supplied to the biomass gasifier 214. Syngas may be a mixture of carbon monoxide and hydrogen that can be converted into a large number of organic compounds that are useful as chemical feed stocks, fuels and solvents.

The torrefaction unit 212 is configured to produce and collect 1) condensable materials with significant fuel blending value, 2) char, and 3) non-condensable gases including C1-4 olefins. The torrefaction unit 212 is configured to route the separated products as follows 1) condensable materials with significant fuel blending value are routed to the gasoline blending unit, 2) char is routed as a feedstock for the biomass gasifier 214, which produces a portion of the syngas components, and 3) non-condensable gases including C1-4 olefins are routed to a catalytic reactor in parallel with biomass gasifier 214 in order to create the other portion of the syngas component to be fed to the methanol synthesis reactor 210.

Torrefaction may be a thermo chemical process used to pre-treat biomass to increase the efficiency of combustion and gasification processes. In this process, biomass is subjected to temperatures of 200-700° C. for ten to sixty minutes to drive off volatile materials, leaving a highly friable solid char material with increased energy density. During the low temperature stages of this thermal decomposition of the biomass, the biomass decomposes into volatile gases and solid char. Biomass is generally made up of a significantly higher amount of volatile matter than coal. For instance, up to 80 percent of the biomass can be volatile matter compared to coal, which is up to 20%.

Note, olefins may be any unsaturated hydrocarbon, such as ethylene, propylene, and butylenes, containing one or more pairs of carbon atoms linked by a double bond. Olefins may have the general formula $CnH2n$, C being a carbon atom, H a hydrogen atom, and n an integer. The olefins are formed during the thermal decomposition (breaking down of large molecules) of the biomass and are useful in the generation of a liquid fuel such as gasoline. Non-condensable olefins containing two to four carbon atoms per molecule (C2-C4) are generally gaseous at ordinary temperatures and pressure; whereas, condensable olefins generally contain five or more carbon atoms (C5+) and are usually liquid at ordinary temperatures and pressure. Cn usually denotes how many carbon molecules are making up the hydrocarbon compound.

The torrefaction unit 212 has two or more areas to segregate out and then route the non-condensable gases including the C1 to C4 olefins, as well as other gases including CO, CH4, CO2 and H2, through a supply line to the catalytic converter 216 that catalytically transform portions of the non-condensable gases to the syngas components of CO, H2, CO2 in small amounts, and potentially CH4 that are sent in parallel with the portion of syngas components from the biomass gasifier 214 to a combined input to the methanol synthesis reactor. The catalytic converter 216 has a control system to regulate a supply of an oxygenated gas and steam along with the non-condensable gases to the catalytic converter 216, which produces at least H2, and CO as exit gases. The catalytic converter 216 uses the control system and the composition of a catalyst material inside the catalytic converter 216 to, rather than convert the supplied non-condensable gases completely into CO2 and H2O in the exit gas, the non-condensable gases, steam, and oxygenated gas are passed through the catalytic converter 216 in a proper ratio to achieve an equilibrium reaction that favors a production of carbon monoxide (CO) and hydrogen (H2) in the exit gas; and thus, reclaim the valuable Renewable Identification Number (RIN) credits associated with the non-condensable gases. RIN credits are a numeric code that is generated by the producer or importer of renewable fuel representing gallons of renewable fuel produced using a renewable energy crop, such as biomass. The primary negative of torrefaction in prior suggestions is the loss of carbon and the associated RIN credits in the volatile materials removed by torrefaction.

The one or more catalytic converters may use a catalytic conversion process that oxidizes the incoming olefins as follows: $CnH2n+[3nO2+1O2]/2 \rightarrow xCO2+xCO+x+1H2O$. For example, when the control system rapidly alternates the air to C1 to C4 non-condensable gas input into the catalytic converter 216, then the reaction runs heavy or lean of stoichiometry. By doing this the carbon monoxide and oxygen present in the exhaust gas from the converter alternates with the air to C1-C4 non-condensable ratio. When the air to C1-C4 non-condensable ratio is richer than stoichiometry, the carbon monoxide content of the exhaust gas rises and the oxygen and carbon dioxide content falls. Catalyst materials inside the converter 216, such as platinum/palladium/Rhodium/ and Cerium, may be used to promote the equilibrium reaction that favors a production of carbon monoxide (CO) and hydrogen (H2) in the exit gas. The cerium may store and release oxygen during these reactions. In the catalytic converter 216, the chemical catalyst material is used but not consumed to augment the chemical reaction.

The system is designed to remove the C1-C4 materials from the volatile stream and then blend the remaining C5+ materials in the stream directly into gasoline. This is beneficial to the finished gasoline product to increase its octane rating as the condensable blendable materials are largely olefins and branched hydrocarbons (CnH2n+2), which typically have higher octane ratings. There are some heavier materials, C25+, which may need to be removed by the filters, depending on the actual quantities in commercial production and type of biomass material being utilized by the integrated plant. Gasoline may be a complex mixture of potentially hundreds of different hydrocarbons. Most of the hydrocarbons are saturated and contain 4 to 12 carbon atoms per molecule.

Biomass gasification is used to decompose the complex hydrocarbons of biomass into simpler gaseous molecules, primarily hydrogen, carbon monoxide, and carbon dioxide. Some char, mineral ash, and tars are also formed, along with methane, ethane, water, and other constituents. The mixture of raw product gases vary according to the types of biomass feedstock used and gasification processes used. The product gas must be cleaned of solids, tars, and other contaminants sufficient for the intended use.

A sulfur filter and other filters between the torrefaction unit 212 and the catalytic converter 216 receive the non-condensable gases collected and routed from the torrefaction unit 212. The hydro treater sulfur filter and other filters are configured to remove contaminants from the stream of non-condensable gases that would inactivate or otherwise harm the catalyst material within the catalytic converter 216. This may include sulfur compounds (e.g. H2S, mercaptans), nitrogen compounds (e.g. NH3, HCN), halides (e.g. HCL), and heavy organic compounds that are known collectively as "tar". Next, depending on the catalyst being used and the product being made, the ratio of hydrogen to carbon monoxide may need to be adjusted and the carbon dioxide byproduct may also need to be removed.

Referring to FIG. 3, the biomass gasifier has a gas clean up section to clean ash, sulfur, water, and other contaminants from the syngas gas stream exiting the biomass gasifier 314. The syngas is then compressed to the proper pressure needed for methanol synthesis. The syngas from the catalytic converter 316 may connect upstream or downstream of the compression stage.

The synthesis gas of H2 and CO from the gasifier and the catalytic converter 316 exit gases are sent to the common input to the one or more methanol synthesis reactors. In addition, small ballast type tanks at higher pressure than system pressure, one filled with H2 and another filled with CO have an input located at the common input to the one or more methanol synthesis reactors. The exact ratio of Hydrogen to Carbon monoxide can be optimized by a control system receiving analysis from monitoring equipment on the compositions of syngas exiting the biomass gasifier 314 and catalytic converters 316 and causing the ballast tanks to insert H2 or CO to optimize the ratio. The methanol produced by the one or more methanol synthesis reactors is then processed in a methanol to gasoline process.

The liquid fuel produced in the integrated plant may be gasoline or another such as diesel, jet fuel, or some alcohols.

The torrefaction unit 312 may have its own several discrete heating stages. Each heating stage is set at a different operating temperature, rate of heat transfer, and heating duration, within the unit in order to be matched to optimize a composition of the non-condensable gases and condensable volatile material produced from the biomass in that stage of the torrefaction unit 312. Each stage has one or more temperature sensors to supply feedback to a control system for the torrefaction unit 312 to regulate the different operating temperatures and rates of heat transfer within the unit.

Volatiles and char may be produced by slow pyrolysis of wood via the process as follows:
- The compositions and yields of volatile products are different in different temperature ranges. Insert all biomass materials
- The composition of volatile products from hardwoods is essentially the same in other hardwoods, as the volatiles from softwoods are essentially comparable as other soft woods, but volatiles from softwoods differ from volatiles from hardwoods.
- Slow pyrolysis at moderate temperatures is preferred to maximize the production of gas and char.
- Rapid pyrolysis at high temperatures is preferred to maximize the production of liquid and minimize char.
- The process is endothermic up to approximately 280° C., at which point an exothermic reaction begins and continues to a temperature of approximately 380° C., where the process once again trends back to endothermic.

The stages of carbonization of wood in six phases in an example torrefaction unit are summarized in Table 1 in FIG. 4. A separation of the mixture of volatile materials occurs in these six stages. Note, a similar set of off-gases can occur if the TMP process uses steam temperatures of 200 degrees C. or more.

The effects of flash, fast, and slow pyrolysis differ on the composition of volatile products obtained at different temperature ranges, room temperature-300° C., 300-400° C., and 400-500° C. Within a specific temperature range, flash, fast, and slow pyrolysis produce different volatile products within each range, consistent with the stages, but the overall list of all the compounds obtained from wood by using different heating rates were the same. Distillation curves for a composition of extractives from hardwood, softwood, and TMP pulp may differ in the percent generation of Non-condensables, Condensables, and Char at different temperatures, rates of heating, and durations of heating. Thus, softwood can be heated in different stages such as 200 degrees C., 200-300, 300-400, 400-500, 500-600, 600-700, and 700 to 800. Hardwood and Thermal mechanical pulp can also be heated in these different stages to obtain a different composition and yield of extractives from the hardwood, softwood, and TMP pulp. The volatile materials from these different biomass types and processes may be used as feed stocks.

Figure 5:
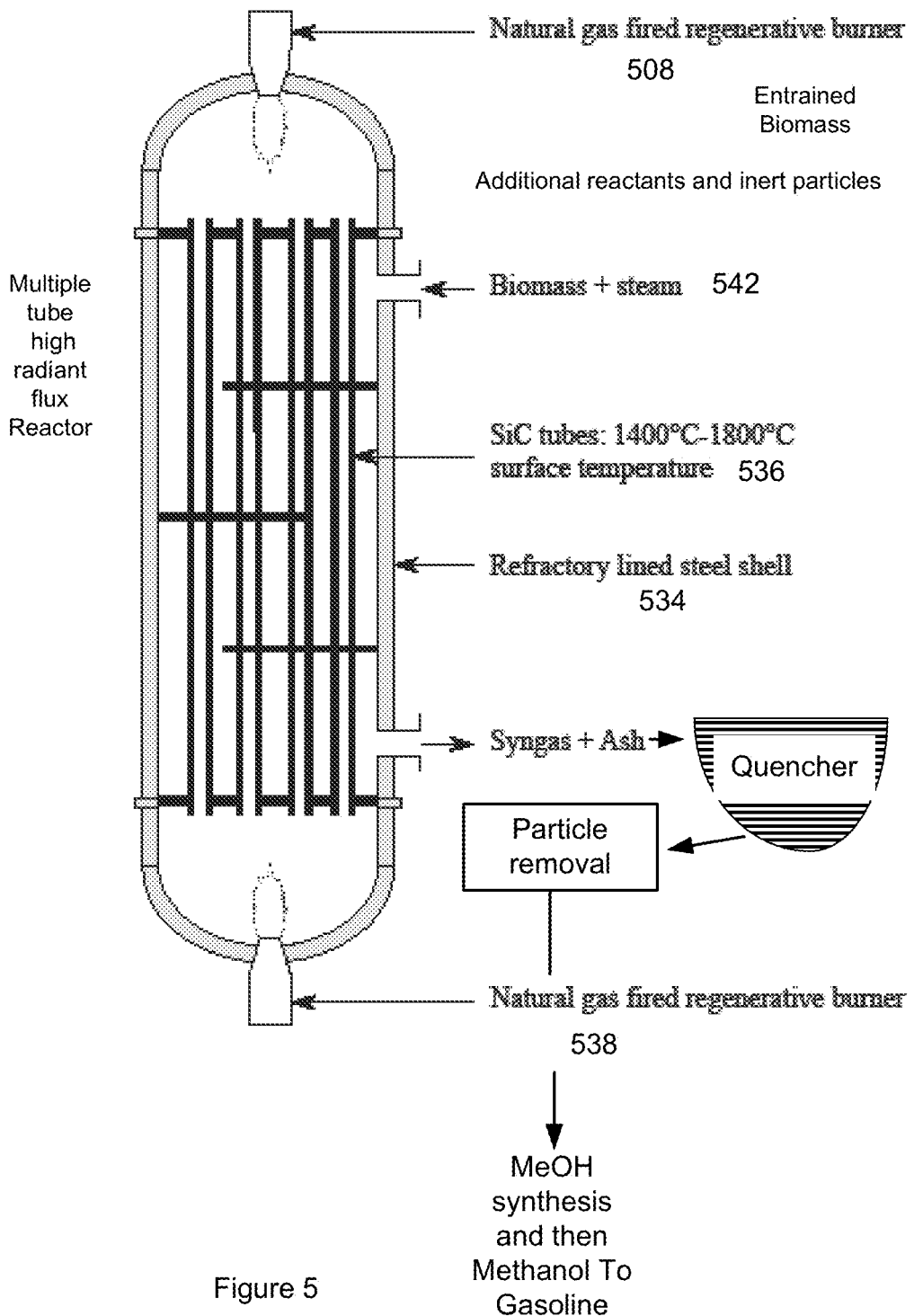
FIG. 5 illustrates a flow schematic of an embodiment for the radiant heat chemical reactor configured to generate chemical products including synthesis gas products.

FIG. 5 illustrates a flow schematic of an embodiment for the radiant heat chemical reactor configured to generate chemical products including synthesis gas products. The multiple shell radiant heat chemical reactor 514 includes a refractory vessel 534 having an annulus shaped cavity with an inner wall. The radiant heat chemical reactor 514 has two or more radiant tubes 536 made out of a solid material. The one or more radiant tubes 536 are located inside the cavity of the refractory lined vessel 534.

The exothermic heat source 538 heats a space inside the tubes 536. Thus, each radiant tube 536 is heated from the inside with an exothermic heat source 538, such as regenerative burners, at each end of the tube 536. Each radiant tube 536 is heated from the inside with fire and gases from the regenerative burners through heat insertion inlets at each end of the tube 536 and potentially by one or more heat insertion ports located in between the two ends. Flames and heated gas of one or more natural gas fired regenerative burners 538 act as the exothermic heat source supplied to the multiple radiant tubes at temperatures between 900° C. and 1800° C. and connect to both ends of the radiant tubes 536. Each tube 536 may be made of SiC or other similar material.

One or more feed lines 542 supply biomass and reactant gas into the top or upper portion of the chemical reactor 514. The feed lines 542 for the biomass particles and steam enter below the entry points in the refractory lined vessel 534 for the radiant tubes 536 that are internally heated. The feed lines 112 are configured to supply chemical reactants including 1) biomass particles, 2) reactant gas, 3) steam, 4) heat transfer aid particles, or 5) any of the four into the radiant heat chemical reactor. A chemical reaction driven by radiant heat occurs outside the multiple radiant tubes 536 with internal fires. The chemical reaction driven by radiant heat occurs within an inner wall of a cavity of the refractory lined vessel 534 and an outer wall of each of the one or more radiant tubes 536.

The chemical reaction may be an endothermic reaction including one or more of 1) biomass gasification ($CnHm+H2O \rightarrow CO+H2+H2O+X$), 2) and other similar hydrocarbon decomposition reactions, which are conducted in the radiant heat chemical reactor 514 using the radiant heat. A steam ($H2O$) to carbon molar ratio is in the range of 1:1 to 1:4, and the temperature is high enough that the chemical reaction occurs without the presence of a catalyst.

The torrefied biomass particles used as a feed stock into the radiant heat reactor design conveys the beneficial effects of increasing and being able to sustain process gas temperatures of excess of 1300 degrees C. through more effective heat transfer of radiation to the particles entrained with the gas, increased gasifier yield of generation of syngas components of carbon monoxide and hydrogen for a given amount of biomass fed in, and improved process hygiene via decreased production of tars and C2+ olefins. The control system for the radiant heat reactor matches the radiant heat transferred from the surfaces of the reactor to a flow rate of the biomass particles to produce the above benefits.

The control system controls the gas-fired regenerative burners 538 to supply heat energy to the chemical reactor 514 to aid in causing the radiant heat driven chemical reactor to have a high heat flux. The inside surfaces of the chemical reactor 514 are aligned to 1) absorb and re-emit radiant energy, 2) highly reflect radiant energy, and 3) any combination of these, to maintain an operational temperature of the enclosed ultra-high heat flux chemical reactor 514. Thus, the inner wall of the cavity of the refractory vessel and the outer wall of each of the one or more tubes 536 emits radiant heat energy to, for example, the biomass particles and any other heat-transfer-aid particles present falling between an outside wall of a given tube 536 and an inner wall of the refractory vessel. The refractory vessel thus absorbs or reflects, via the tubes 536, the concentrated energy from the regenerative burners 538 positioned along on the top and bottom of the refractory vessel to cause energy transport by thermal radiation and reflection to generally convey that heat flux to the biomass particles, heat transfer aid particles and reactant gas inside the chemical reactor. The inner wall of the cavity of the thermal refractory vessel and the multiple tubes 536 act as radiation distributors by either absorbing radiation and re-radiating it to the heat-transfer-aid particles or reflecting the incident radiation to the heat-transfer-aid particles. The radiant heat chemical reactor 514 uses an ultra-high heat flux and high temperature that is driven primarily by radiative heat transfer, and not convection or conduction.

Convection biomass gasifiers used generally on coal particles typically at most reach heat fluxes of 5-10 $kW/m^2$. The high radiant heat flux biomass gasifier will use heat fluxes significantly greater, at least three times the amount, than those found in convection driven biomass gasifiers (i.e. greater than 25 $kW/m^2$). Generally, using radiation at high temperature (>950 degrees C. wall temperature), much higher fluxes (high heat fluxes greater than 80 $kW/m^2$) can be achieved with the properly designed reactor. In some instances, the high heat fluxes can be 100 $kW/m^2$-250 $kW/m^2$.

Next, the various algorithms and processes for the control system may be described in the general context of computer-executable instructions, such as program modules, being executed by a computer. Generally, program modules include routines, programs, objects, components, data structures, etc. that perform particular tasks or implement particular abstract data types. Those skilled in the art can implement the description and/or figures herein as computer-executable instructions, which can be embodied on any form of computer readable media discussed below. In general, the program modules may be implemented as software instructions, Logic blocks of electronic hardware, and a combination of both. The software portion may be stored on a machine-readable medium and written in any number of programming languages such as Java, C++, C, etc. The machine-readable medium may be a hard drive, external drive, DRAM, Tape Drives, memory sticks, etc. Therefore, the algorithms and controls systems may be fabricated exclusively of hardware logic, hardware logic interacting with software, or solely software.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms may be written in a number of different software programming languages. Also, an algorithm may be implemented with lines of code in software, configured logic gates in electronic circuitry, or a combination of both. The control system uses the software in combination with integrated logic chips in hardware to control the system.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

While some specific embodiments of the invention have been shown the invention is not to be limited to these embodiments. For example, the recuperated waste heat from various plant processes can be used to pre-heat combustion air, or can be used for other similar heating means. Regenerative gas burners or conventional burners can be used as a heat source for the furnace. Alcohols C1, C2 and higher as well as ethers that are formed in the torrefication process may be used as a high value in boosting the octane rating of the generated liquid fuel, such as gasoline. Biomass gasifier reactors other than a radiant heat chemical reactor may be used. The Steam Methane Reforming may be/include a SHR (steam hydrocarbon reformer) that cracks short-chained hydrocarbons (<C20) including hydrocarbons (alkanes, alkenes, alkynes, aromatics, furans, phenols, carboxylic acids, ketones, aldehydes, ethers, etc, as well as oxygenates into syngas components. The invention is to be understood as not limited by the specific embodiments described herein, but only by scope of the appended claims.

The invention claimed is:

1. An integrated plant configured to generate a syngas and make use of the syngas to generate a fuel, comprising:
   a thermal pretreatment unit that includes
   a source of biomass,
   a source of steam,
   an input cavity configured to receive biomass as a feedstock from the source of biomass, the biomass having a plurality of cellulose fibers,
   a steam supply input configured to receive steam from the source of steam,
   and two or more stages operably coupled with each other, where the steam supply input is coupled to the two or more stages, where the two or more stages are configured to pretreat the biomass for subsequent supply to a biomass gasifier operably coupled downstream from an exit of the stages, where the stages are configured to pretreat the received biomass by applying a combination of heat, pressure, moisture, and mechanical agitation to make the received biomass into a pulp form, where the thermal pretreatment unit is configured to at least partially break down a bulk structure of the received biomass by applying steam from the steam supply input to degrade bonds of the received biomass between a lignin component and a hemi-cellulose component from the plurality of cellulose fibers in order to produce particles of biomass from the exit of the two or more stages of the thermal pretreatment unit; and
   where the biomass gasifier includes
   a reactor configured to react the particles of the biomass broken down by the pretreatment from the two or more stages of the thermal pretreatment unit,
   a feed section of the biomass gasifier configured to receive the particles of biomass produced by the thermal pretreatment unit and feed the particles into the reactor through one or more feed lines,
   a high-temperature steam supply input,
   at least one gas-fired heater, and
   where the reactor is configured to react the particles of biomass in the presence of steam from the high-temperature steam supply input, by way of a rapid biomass gasification reaction, at a temperature of at least approximately 700° C., to create components of the syngas, including hydrogen ($H_2$) and carbon monoxide (CO), which are then collected at an exit of the reactor and subsequently fed for further processing to an input of a downstream methanol ($CH_3OH$) synthesis reactor to produce methanol; and
   where the at least one gas-fired heater couples to the reactor and cooperates with the steam from the high-temperature steam supply input to supply heat energy and control the temperature of the reactor to at least approximately 700° C., wherein the thermal pretreatment unit, the biomass gasifier, and the downstream methanol synthesis reactor make up at least part of the integrated plant.

2. The integrated plant of claim 1, further comprising:
   wherein the two or more stages of the thermal pretreatment unit includes a steam tube stage and a refiner unit stage,
   wherein the steam tube stage includes an input cavity configured to receive the received biomass in chip form,
   wherein the steam supply input is configured to apply the steam into a vessel containing the received biomass in chip form at an elevated temperature in a range of approximately 130° C. to approximately 200° C. at a pressure in a range of approximately 70 psi and approximately 110 psi,
   wherein the refiner unit stage is configured to receive the biomass chips with softened lignin from the steam tube stage, the refiner unit stage which is configured to apply the mechanical agitation to the biomass chips.

3. The integrated plant of claim 1,
   wherein the two or more stages of the thermal pretreatment unit include a steam tube stage and a refiner unit stage,
   wherein the steam tube stage is configured to apply the steam to the biomass at a temperature in a range greater than approximately a glass transition point of lignin for softening the lignin,
   wherein the steam tube stage is configured to receive the plurality of biomass chips, the plurality of biomass chips comprising leaves, needles, bark, and wood, and is configured to heat the plurality of biomass chips, by way of the steam, at a temperature in a range greater than approximately 150° C. and at a pressure in a range greater than approximately 70 psi, and
   where a torrefaction unit is located between the exit of the two or more stages of the thermal pretreatment unit and the biomass gasifier, where the torrefaction unit is configured to at least partially pyrolize the particles of the biomass broken down by the pretreatment from the two or more stages at a temperature in a range of less than approximately 700° C. for a preset duration for forming off-gases for further use in forming a portion of at least one syngas component.

4. The integrated plant of claim 1, where the two or more stages of the thermal pretreatment unit include at least a thermally decomposing stage and a refiner unit stage, where the thermally decomposing stage has the input cavity to receive chips of the biomass and a control system configured to control a low-pressure steam supply input to apply steam into a vessel containing the chips of biomass at an elevated temperature of 100 to 150 degrees C. at a pressure around atmospheric for a set period of time, where the thermal pretreatment unit is configured to then feed chips of biomass with softened lignin from the thermally decomposing stage to a second stage containing the refiner unit stage with its higher pressure to further separate the cellulose fibers of the biomass and internally pressurize any liquids and gases within the biomass; and
   where in the second stage containing the refiner unit stage of the Thermo Mechanical Pulping unit, the control system is configured to raise the pressure and temperature in a chamber containing the chips of biomass with softened lignin to an increased temperature of at least twenty degrees greater than an operating environment of the vessel with chips of biomass in the thermally decomposing stage and to an increased pressure greater than three times atmospheric in the chamber but for a shorter duration than the set period of time in the thermally decomposing stage, where internally in the refiner unit stage, a mechanical agitation mechanism is configured to apply mechanical force to apply the mechanical agitation to assist the higher pressure steam in physically tearing the cellulose fibers while the heat and pressure of the steam expands and blows apart the structure of the lignin, fiber, and hemi-cellulose in order to produce a size of the particles of biomass of an equivalent spherical diameter of less than 3 mm after exiting the thermal pretreatment unit, which should be more easily and rapidly gasified in the reactor vessel.

5. The integrated plant of claim 2,
wherein the refiner unit stage further includes an outlet and a collection chamber disposed at the outlet, the collection chamber configured to collect the plurality of biomass particles, comprising a pulp structure, for facilitating rapid gasification,
wherein the pulp structure includes at least one form of an elongated form, a torn elongated form, and a shredded elongated form, and
wherein the plurality of biomass particles includes a surface-to-volume ratio greater than that of the plurality of biomass chips of a same mass for facilitating heat transfer, accelerating thermal decomposition, and accelerating gasification thereof.

6. The integrated plant of claim 2,
wherein the refiner unit stage a knife stage configured to initially chop the plurality of cellulose fibers in the biomass to a length in a range of approximately 1 mm to approximately 3 mm;
a high pressure steam stage for further facilitating blowing-apart of the grouped fibers in the biomass, and
where the refiner unit stage produces fiber particles that on average have an equivalent spherical diameter of less than 3 mm.

7. The integrated plant of claim 5, further comprising a conveying system coupled with the collection chamber for transferring the plurality of biomass particles,
wherein the plurality of stages of the thermal pretreatment unit is configured to loosen and strip a plurality of fibers from the lignin in the biomass, and
wherein the plurality of stages facilitates maintaining a majority of the initial lignin and cellulose of the biomass received in the receiver section of the thermally decomposing stage in the plurality of biomass particles as substantially separated from the plurality of cellulose fibers in the pulp form in the collection chamber.

8. The integrated plant of claim 2, further comprising a chipper unit,
wherein a thermally decomposing stage and a refiner unit stage of the thermal pretreatment unit are configured to receive and process at least one cellulose material of wood, bark leaves, and needles from the chipper unit,
wherein the refiner unit stage is configured to process the at least one cellulose material into a pulp and to subsequently transfer the pulp, as the plurality of biomass particles, into the biomass gasifier for conversion into at least one syngas component in a rapid biomass gasification reaction, and
wherein the thermal pretreatment unit includes a thermo-mechanical pulping unit.

9. The integrated plant of claim 7, further comprising:
a collection tank,
a methanol synthesis reactor,
wherein the collection chamber is configured to collect the plurality of biomass particles, comprising the pulp structure,
wherein the conveyor system is configured to transfer the plurality of biomass particles, comprising the pulp structure, to the torrefaction unit for pyrolizing thereof at a temperature in a range of less than approximately 700° C. for a preset duration for forming off-gases for further use in forming a portion of at least one syngas component, and
wherein the collection tank is configured to receive and store the at least one syngas component for eventual processing by the methanol synthesis reactor.

10. The integrated plant of claim 1, further comprising:
a water separation unit;
a cyclone unit;
a conveying system;
a filter unit;
a gasoline (MTG) reactor;
a methanol synthesis reactor,
wherein a collection chamber disposed at an outlet stage of the refiner unit stage is configured to collect and transfer the biomass reduced into smaller particle sizes to the water separation unit, and
wherein the cyclone unit is configured to remove water from the particles,
wherein the conveying system is configured to transfer at least one of the plurality of loose fibers, the separated lignin, and the cellulose to the torrefaction unit for torrefaction and pyrolization thereto at a temperature in a range of less than approximately 700° C. for a preset duration,
wherein the filter unit is configured to separate condensable hydrocarbons from the water removed from the pulp,
wherein the methanol synthesis reactor is configured to receive and transfer methanol, which is derived from the syngas components in a stoichiometric ratio, and
a methanol to gasoline (MTG) reactor configured to receive the methanol and generate gasoline.

11. The integrated plant of claim 2,
wherein the refiner unit stage includes a collection chamber configured to collect and transfer the plurality of biomass particles with separated fiber to a feeding system for the biomass gasifier,
wherein the thermal pretreatment unit is configured to receive a plurality of types of biomass,
wherein the plurality of types of biomass includes at least one of a soft wood, a hard wood, a grass, a plant hull, and any cellulose material capable of being blended and thermo-mechanically processed into a homogenized torrefied feedstock within the thermal pretreatment unit that is subsequently collectable and transferable into the biomass gasifier, and
wherein the torrefaction unit is configured to facilitate flexibility of operation in relation to at least one of a pre-existing feed supply equipment and a pre-existing biomass gasifier via at least particle size control of the plurality of biomass particles produced by the refiner unit stage.

12. The integrated plant of claim 1, further comprising a control system,
wherein the biomass gasifier includes a radiant heat reactor configured to transfer radiant heat to the plurality of biomass particles flowing therethrough, whereby the plurality of biomass particles entrained in the flow are heated in a temperature range greater than approximately 900° C. to approximately 1300° C. for producing the at least one syngas component comprising at least one of carbon monoxide and hydrogen, and whereby production of methane is maintained in a range of ≤1% of a plurality of exit products, wherein the reactor includes a radiant heat reactor, the radiant heat reactor configured to convey effective heat transfer by radiation to the plurality of biomass particles and to facilitate increasing a gasifier yield comprising at least one syngas component of carbon monoxide and hydrogen for a given amount of input biomass, and to facilitate improving process hygiene by decreasing production of tars and $C_2+$ olefins in relation to that of a plurality of biomass chips, wherein the control system is configured to match the radiant heat transferred from a surface of the reactor to a flow rate of the plurality of biomass particles, whereby a gasifier yield is optimizable.

* * * * *